(12) United States Patent
Chen et al.

(10) Patent No.: US 8,093,068 B2
(45) Date of Patent: Jan. 10, 2012

(54) METHODS FOR USE IN HUMAN-ADAPTING MONOCLONAL ANTIBODIES

(75) Inventors: Shizhong Chen, San Diego, CA (US); Shanrong Zhao, San Diego, CA (US)

(73) Assignee: Centocor, Inc., Malvern, PA (US)

( * ) Notice: Subject to any disclaimer, the term of this patent is extended or adjusted under 35 U.S.C. 154(b) by 408 days.

(21) Appl. No.: 11/924,094

(22) Filed: Oct. 25, 2007

(65) Prior Publication Data

US 2009/0137403 A1 May 28, 2009

Related U.S. Application Data

(60) Provisional application No. 60/863,008, filed on Oct. 26, 2006.

(51) Int. Cl.
*G01N 33/536* (2006.01)
*G01N 33/531* (2006.01)
*C07K 16/00* (2006.01)
(52) U.S. Cl. ...................... 436/536; 436/543; 530/387.1
(58) Field of Classification Search .................. None
See application file for complete search history.

(56) References Cited

U.S. PATENT DOCUMENTS

| | | | |
|---|---|---|---|
| 6,881,557 B2 * | 4/2005 | Foote | 435/69.6 |
| 2005/0042664 A1 * | 2/2005 | Wu et al. | 435/6 |
| 2005/0048578 A1 * | 3/2005 | Zhang | 435/7.1 |
| 2005/0148001 A1 * | 7/2005 | Luo et al. | 435/6 |
| 2005/0175986 A1 * | 8/2005 | Gross et al. | 435/5 |
| 2006/0246515 A1 * | 11/2006 | Zhu et al. | 435/7.1 |

FOREIGN PATENT DOCUMENTS

| | | |
|---|---|---|
| WO | WO 96/08564 A1 | 3/1996 |
| WO | WO 05/42743 A2 | 5/2005 |

OTHER PUBLICATIONS

Gonzalez, et al., "Minimizing immunogenicity of the SDR-grafted humanized antibody CC49 by genetic manipulation of the framework residues," Molecular Immunology, 40: 337-349 (20003).
Kashmiri, et al., "SDR grafting—a new approach to antibody humanization," Methods, 36: 25-34 (2005).
Dall'Acqua, et al., "Antibody humanization by framework shuffling," Methods36: 43-60 (2005).
Co, et al., "A Humanized Antibody Specific for the Platelet Integrin gpIIb/IIIa," Journal of Immunology, 152: 2968-2976 (1994).
Gorman, et al., "Reshaping a therapeutic CD4 antibody," Proceedings of the National Academy of Science, 88: 4181-4185 (1991).
Queen, et al., "A humanized antibody that binds to the interleukin 2 receptor," Proceedings of the National Academy of Science, 86: 10029-10033 (1989).
Jones, et al., "Replacing the complementarity-determining regions in a human antibody with those from a mouse," Nature, 321: 522-525 (1986).
Tempest, et al., "Reshaping a Human Monoclonal Antibody to Inhibit Human Respiratory Syncytial Virus Infection in Vivo," Biotechnology, 9: 266-271 (1991).
Altschul, et al., "Basic Local Alignment Search Tool," Journal of Molecular Biology, 215: 403-410 (1990).
Chothia, et al., "Canonical Structures for the Hypervariable Regions of Immunoglobulins," Journal of Molecular Biiology, 196:901-917 (1987).
Honegger, et al., "Yet Another Numbering Scheme for Immunoglobulin Variable Domains: An Automatic Modeling and Analysis Tool," Journal of Molecular Biology, 309: 657-670 (2001).
Jirholt, et al., "Exploiting sequence space: shuffling in vivo formed complementarity determining regions into a master framework," Gene, 215:471-476 (1998).
Lazar, et al., "A molecular immunology approach to antibody humanization and functional optimization," Molecular Immunology, 44:1986-1998 (2007).
MacCallum, et al., "Antibody-antigen Interactions: Contact Analysis and Binding Site Topography," Journal of Molecular Biology, 262:732-745 (1996).
Dr. Andrew C.R. Martin, "Antibodies, Abysis Database," Dr. Andrew C.R. Martin's Group at UCL, Internet Site Address: http://www.bioinf.org.uk/abs/, (Nov. 9, 2009).
Morea, et al., "Antibody Structure, prediction and redesign," Biophysical Chemistry, 68:9-16 (1997).
Tramontano, et al, "Framework Residue 71 is a Major Determinant of the Position and Conformation of the Second Hypervariable Region in the $V_h$ Domains of Immunoglobulins," Journal of Molecular Biology, 215: 175-182 (1990).
Wu, et al., "Humanization of a Murine Monoclonal Antibody by Simultaneous Optimization of Framework and CDR Residues," Journal of Molecular Biology, 294:151-162 (1999).
Zhao, et al., "Molecular Immunology," Molecular Immunology, 47:694-700 (2010).

* cited by examiner

*Primary Examiner* — Anne M. Gussow
(74) *Attorney, Agent, or Firm* — Kirk Baumeister

(57) ABSTRACT

Methods useful for human adapting non-human monoclonal antibodies are disclosed. The methods select candidate human antibody framework sequences from a human germline framework database.

7 Claims, 10 Drawing Sheets

Fig. 1

```
                Eu  SPE    EYNGGLVTVSS
                            |    ||||
   mouse anti-Tac  FDY    WGQGTTLTVSS
                   |||    |||||   ||||
       human J_H 4 FDY    WGQGTLVTVSS
                   |||    |||||||||||
humanized anti-Tac FDY    WGQGTLVTVSS

CDR3      FW4
```

Fig. 2

$J_H1$     AEYFQHWGQGTLVTVSS $J_H2$     YWYFDLWGRGTLVTVSS $J_H3$          AFDVWGQGTMVTVSS $J_H4$         YFDYWGQGTLVTVSS $J_H5$        NWFDSWGQGTLVTVSS $J_H6$   YYYYYGMDVWGQGTTVTVSS

Fig. 5

Amino Acid sequence for 1068 heavy chain variable region

MGWSYIILFLVATATDVHSQVQLQQPGAELVQPGTSVRLSCKASGYIFTTYWIHWVKQRPGQGLEWIGE
INPNNGRINYNEKFKTKATLTVDKSSSTAYMQLSSLTSEDSAVYYCTRVGVMITTFPYWGQGTLVTVSA

FR1:     QVQLQQPGAELVQPGTSVRLSCKASGYIFT

CDR1:    TYWIH

FR2:     WVKQRPGQGLEWIG

CDR2:    EINPNNGRINYNEKFKT

FR3:     KATLTVDKSSSTAYMQLSSLTSEDSAVYYCTR

CDR3:    VGVMITTFPY

FR4:     WGQGTLVTVSA

Fig. 6

Amino Acid sequence for 1068 light chain variable region
MSVLTQVLALLLLWLTGARCDIQMTQSPASLSASVGETVTITCRASGNIHNYLAWYQQKQGKSPQLLVY
NAKTLADGVPSRFSGSESGTQYSLKINSLQPEDFGSYYCQHFWSTPFTFGSGTKLELK

FR1:      DIQMTQSPASLSASVGETVTITC

CDR1:       RASGNIHNYLA

FR2:      WYQQKQGKSPQLLVY

CDR2:       NAKTLAD

FR3:      GVPSRFSGSESGTQYSLKINSLQPEDFGSYYC

CDR3:       QHFWSTPFT

FR4:      FGSGTKLELK

Fig. 7

```
            ------------FR1---------------   ------FR2------
HV1    QVQLVQSGAEVKKPGASVKVSCKASGYTFT         WVRQAPGQRLEWMG
HV4    ..............................         ........G.....
HV5    ..............................         .....T..G.....
HV7    ................S..........G..S        ........G.....

---------------FR3---------------   ----FR4----
HV1    RVTITRDTSASTAYMELSSLRSEDTAVYYCAR        WGQGTLVTVSS
HV4    ...M.....I........R...D.........        ...........
HV5    ...M..N..I......................        ...........
HV7    .....A.E.T......................        ..R........
```

Fig. 8

```
           ----------FR1-----------     ------FR2------
    LV1    DIQMTQSPSSLSASVGDRVTITC      WYQQKPGKAPKLLIY
    LV3    .......................     ............R..
    LV5    .......................     ..........V....
    LV7    .......................     .F.........S...

----------------FR3---------------     ---FR4----
    LV1    GVPSRFSGSGSGTDFTLTISSLQPEDFATYYC       FGQGTKLEIK
    LV3    ...............E................       ..........
    LV5    ............................V...       ..G...V...
    LV7    ................................       ..........
```

METHODS FOR USE IN HUMAN-ADAPTING MONOCLONAL ANTIBODIES

CLAIM TO RIGHT OF PRIORITY

The present application claims priority to U.S. Provisional Application Ser. No. 60/863,008, filed 26 Oct. 2006, the entire contents of which is incorporated herein by reference in its entirety.

FIELD OF THE INVENTION

This invention relates to methods for selecting human variable region frameworks for use in human adaptation of non-human monoclonal antibodies such as rodent antibodies.

BACKGROUND OF THE INVENTION

Antibody human adaptation is a generic term describing the engineering of xenogeneic monoclonal antibodies (mAbs) against human therapeutic targets to maximally replace the xenogeneic sequences with human antibody sequences while preserving their antigen-binding specificities. The aim is to reduce the immunogenicity of these antibodies to improve their therapeutic properties and values. The engineered antibodies generated are also known in the art as humanized or CDR-grafted antibodies.

Currently, the most widely used technique for antibody human adaptation is known as "CDR grafting." The scientific basis of this technology is that the binding specificity of an antibody resides primarily within the three hypervariable loops known as the Complementarity Determining Regions (CDRs) of its light and heavy chain variable regions (V-regions), whereas the more conserved framework regions (framework, FW; framework region, FR) provide structure support function. By grafting the CDRs to an appropriately selected FW, some or all of the antibody-binding activity can be transferred to the resulting recombinant antibody. The first demonstration of the transfer of specificity by CDR grafting was for a hapten nitrophenol (NP) (Jones et al., *Nature* 321: 522-525 (1986)).

Since the methodology for defining CDRs has been well established, the key to CDR grafting is the selection of a most appropriate human antibody acceptor for the graft. Various strategies have been developed to select human antibody acceptors with the highest similarities to the amino acid sequences of donor CDRs or donor FW, or to the donor structures. All these "best fit" strategies, while appearing very rational, are in fact based on one assumption, i.e., a resulting recombinant antibody that is most similar (in amino acid sequence or in structure) to the original antibody will best preserve the original antigen binding activity. While these strategies have all been successfully applied to generate therapeutic antibodies (e.g., Tempest et al., *Biotechnology*. 9:266-71 (1991), Gorman et al., *Proc Natl Acad Sci USA* 88:4181-4185 (1991), Co et al., *J Immunol*. 152:2968-76 (1994)), the underlying hypothesis has never been seriously tested.

One potential problem of the best-fit strategies is that the criteria of best fits are mathematical, but not necessarily biological. The fitness measured by the degree of homology, for example, is the sum of numerical values assigned to identical, homologous, and dissimilar amino acid residues or nucleic acid sequences. Although these assigned values have largely been validated in many other homology evaluating systems, the fine differences that may not be significant for other systems could be important for calculating the best fits in antibody human adaptation.

A related problem is, given two acceptors with identical or very close degree of total fitness for the donor, their local fitness in different FRs may be different. Can one region be more important than the other? How will that be determined? In short, a mathematic model has not yet been validated to satisfy the requirement of calculating the best fits in donor-acceptor relationship in antibody engineering.

A further complication relates to the interactions between the two chains of an antibody: a best-fit heavy chain acceptor and a best-fit light chain acceptor may not fit with each other to best conserve the binding activity of the donor. No tool is available to evaluate interchain fitness. Investigators have paired heavy and light chains of several antibodies against a same epitope to try to find a better pairing. However, this has not been attempted in antibody human adapatation.

In theory, all human germline sequences have been sequenced and are available for antibody FW searching. In practice, however, the majority of human V regions that have been used so far in antibody humanization are from mature antibody genes, often those of myeloma proteins. They are likely to contain somatic mutations. These mutations are unique to the individual from which the rearranged genes were derived, and hence will be seen as foreign by other individuals. Germline database sequences are more suitable for antibody humanization from this perspective. However, no germline database sequences encoding the whole FW are readily available for antibody humanization, and they can only be generated by combination of raw V and J gene sequences.

Another problem of using mature antibody genes for acceptor FW is that not all of the potential V-J combinations for light chain or V-D-J combinations for heavy chain are represented in the mature genes. Thus, situations can arise in which a closely matching V gene is linked to a poorly matching J segment. The humanization of the mouse anti-Tac monoclonal antibody described by Queen et al., (*Proc Natl Acad Sci USA* 86:10029-10033 (1989)) is an example. Comparison of the anti-Tac $V_H$ region to the NBRF-PIR database (http://www_.psc._edu/general/software/packages/nbrf-pir/nbrf._html) indicated that the $V_H$ region of the human myeloma protein Eu had the highest degree of homology (57% identical over $VDJ_H$). However, framework 4 of the Eu $V_H$ region has several amino acids, presumably encoded by the Eu $J_H$ segment, that are atypical of human $J_H$ segments. This resulted in a poor match between the Eu framework 4 and that of anti-Tac (FIG. 1). Separate comparison of the anti-Tac $J_H$ region (framework 4 and the framework 4—proximal end of CDR3) to the amino acid sequences of the known functional human $J_H$ segments (of which there are 6; see FIG. 2) indicates that human $J_H4$ is a much better-match than the Eu $J_H$. This example suggests that separate comparisons of V and J elements are more advantageous than comparison of the whole variable regions between rodent and human antibody sequences. Currently, a tool for this type of separate comparison is not readily available.

Not all amino acids in the CDRs are involved in antigen binding. Thus, it has been proposed that the grafting of only those residues that are critical in antigen-antibody interaction—the so-called specificity determining residues grafting (SDR-grafting)—will further increase the content of human antibody sequences in the resulting recombinant antibody (Kashmiri et al., *Methods*. 36:25-34 (2005); Gonzales et al., *Mol Immunol*. 40:337-49 (2004)). The application of this strategy requires information on the antibody structure as well as antibody-antigen contact residues, which are quite often unavailable. Even when such information is available, there is no systematic method to reliably identify the SDRs, and SDR-grafting remains so far mostly at the basic research level.

Recently, a novel strategy called "human framework shuffling" has been developed (Dall'Acqua et al., *Methods* 36:43-60 (2005). This technique works by ligating DNA fragments encoding CDRs to DNA fragments encoding human FR1, FR2, FR3, and FR4, thus generating a library of all combinations between donor CDRs and human FRs. While this strategy has been successfully applied, there are two potential problems. First, the FRs of the resulting antibody, while all of human sources, are likely to be from non-contiguous FWs, and therefore unnatural. It remains to be seen whether these unnatural FWs will be immunogenic in humans. Second, the library, in theory, can be prohibitively large, and places a high demand on screening and assay resources.

Thus, a need exists for improved methods for making human-adapted antibodies.

BRIEF DESCRIPTION OF THE DRAWINGS

FIG. 1 shows anti-Tac JH region comparisons, reflecting the Eu sequence (SEQ ID NO:17), mouse anti-Tac sequence (SEQ ID NO:18), human $J_H4$ sequence (SEQ ID NO:55) and humanized anti-Tac sequence (SEQ ID NO:19).

FIG. 2 shows the following human JH segment amino acid sequences $J_H1$ (SEQ ID NO:11), $J_H2$ (SEQ ID NO:12), $J_H3$ (SEQ ID NO:13), $J_H4$ (SEQ ID NO:14), $J_H5$ (SEQ ID NO:15) and $J_H6$ (SEQ ID NO:16).

FIG. 5 shows the amino acid sequence for the heavy chain variable region (SEQ ID NO:56) and the corresponding FRs/CDRs for murine anti-TLR3 mAb 1068, wherein the sequence for FR1 is SEQ ID NO:20, CDR1 is SEQ ID NO:21, FR2 is SEQ ID NO:22, CDR2 is SEQ ID NO:23, FR3 is SEQ ID NO:24, CDR3 is SEQ ID NO:25 and FR4 is SEQ ID NO:26.

FIG. 6 shows the amino acid sequence for 1068 light chain variable region (SEQ ID NO:57) and the corresponding FRs/CDRs for murine anti-TLR3 mAb 1068, wherein the sequence for FR1 is SEQ ID NO:27, CDR1 is SEQ ID NO:28, FR2 is SEQ ID NO:29, CDR2 is SEQ ID NO:30, FR3 is SEQ ID NO:31, CDR3 is SEQ ID NO:32 and FR4 is SEQ ID NO:33.

FIG. 7 shows an alignment of heavy chain FW library sequences, reflecting HV1 FR1 (SEQ ID NO:34), HV1 FR2 (SEQ ID NO:36), HV1 FR3 (SEQ ID NO:39), HV1 FR4 (SEQ ID NO:43), HV4 FR1 (SEQ ID NO:34), HV4 FR2 (SEQ ID NO:37), HV4 FR3 (SEQ ID NO:40), HV4 FR4 (SEQ ID NO:43), HV5 FR1 (SEQ ID NO:34), HV5 FR2 (SEQ ID NO:38), HV5 FR3 (SEQ ID NO:41), HV5 FR4 (SEQ ID NO:43), HV7 FR1 (SEQ ID NO:35), HV7 FR2 (SEQ ID NO:37), HV7 FR3 (SEQ ID NO:42) and HV7 FR4 (SEQ ID NO:44).

FIG. 8 shows an alignment of light chain FW library sequences, reflecting LV1 FR1 (SEQ ID NO:45), LV1 FR2 (SEQ ID NO:46), LV1 FR3 (SEQ ID NO:50), LV1 FR4 (SEQ ID NO:53), LV3 FR1 (SEQ ID NO:45), LV3 FR2 (SEQ ID NO:47), LV3 FR3 (SEQ ID NO:51), LV3 FR4 (SEQ ID NO:53), LV5 FR1 (SEQ ID NO:45), LV5 FR2 (SEQ ID NO:48), LV5 FR3 (SEQ ID NO:52), LV5 FR4 (SEQ ID NO:54), LV7 FR1 (SEQ ID NO:45), LV7 FR2 (SEQ ID NO:49), LV7 FR3 (SEQ ID NO:50) and LV7 FR4 (SEQ ID NO:53).

SUMMARY OF THE INVENTION

Figure 3:
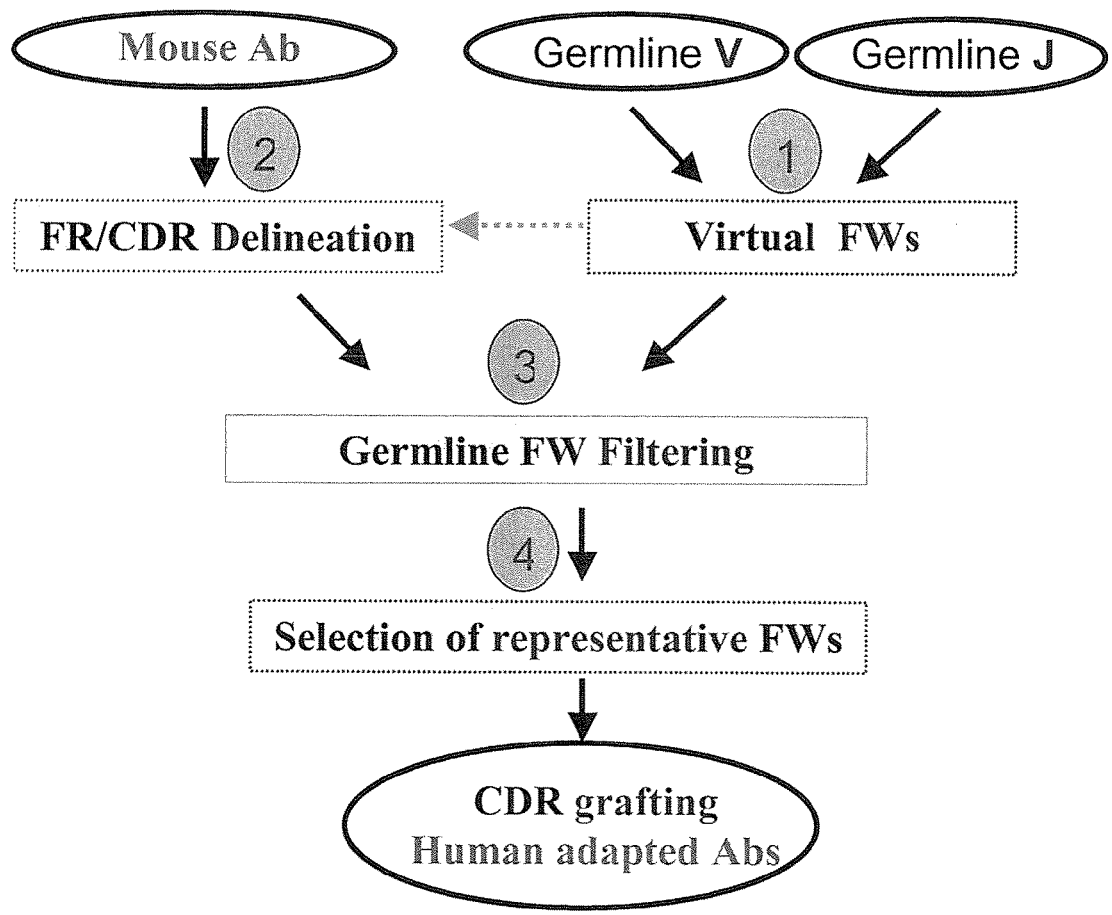
FIG. 3 shows the framework library algorithm flowchart.

One aspect of the invention is a method for selecting human antibody frameworks for use in making a human-adapted antibody comprising the steps of:
a. obtaining a peptide sequence for a variable region of a non-human antibody;
b. delineating the peptide sequences of the complementarity determining regions (CDRs) and framework regions of the non-human variable region;
c. constructing a library of peptide sequences for human antibody framework 1, 2, 3 and 4 regions encoded by human germline genes;
d. selecting a subset of member human peptide sequences from the library having an identical length to the framework regions of the non-human mature antibody;
e. comparing the frame region sequence similarity of the selected human peptide sequences to the peptide sequences of the non-human framework regions;
f. comparing the CDR1 and CDR2 length compatibility between the selected human peptide sequences and the peptide sequences of the non-human framework regions;
g. selecting a second subset of the selected human peptide sequences wherein the peptide sequences selected have a frame region similarity of greater than an identity_threshold value and the sum of the length difference of CDR1 and CDR2 is smaller than or equal to a CDR12_length_compatibility_threshold value; and
h. selecting representative frameworks from the second subset of step g) based upon a library_size value and a framework_region_redundancy value.

Another aspect of the invention is a method of making a human-adapted antibody comprising the steps of:
a. obtaining a peptide sequence for a variable region of a non-human antibody;
b. delineating the peptide sequences of the complementarity determining regions (CDRs) and framework regions of the non-human variable region;
c. constructing a library of peptide sequences for human antibody framework 1, 2, 3 and 4 regions encoded by human germline genes;
d. selecting a subset of member human peptide sequences from the library having an identical length to the framework regions of the non-human mature antibody;
e. comparing the frame region sequence similarity of the selected human peptide sequences to the peptide sequences of the non-human framework regions;
f. comparing the CDR1 and CDR2 length compatibility between the selected human peptide sequences and the peptide sequences of the non-human framework regions;
g. selecting a second subset of the selected human peptide sequences wherein the peptide sequences selected have a frame region similarity of greater than an identity_threshold value and the sum of the length difference of CDR1 and CDR2 is smaller than or equal to a CDR12_length_compatibility_threshold value;
h. selecting representative frameworks from the second subset of step g) based upon a library_size value and a framework_region_redundancy value; and i. constructing a chimeric molecule that includes each of the CDR regions from the non-human variable region and framework regions from at least one member of the human heavy and light chain representative frameworks selected in step h), wherein the chimeric molecule is a human-adapted antibody or antibody fragment that binds the same antigen as that bound by the non-human antibody.

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise. Thus, for example, reference to "a peptide chain" is a reference to one or more peptide chains and includes equivalents thereof known to those skilled in the art.

Unless defined otherwise, all technical and scientific terms used herein have the same meaning as commonly understood by one of ordinary skill in the art to which this invention belongs. Although methods similar or equivalent to those described herein can be used in the practice or testing of the invention, exemplary methods are described herein.

The term "antibody" means immunoglobulin or antibody molecules and antibody fragments. In general, antibodies are proteins or polypeptides that exhibit binding specificity to a specific antigen. Intact antibodies are heterotetrameric glycoproteins, composed of two identical light chains and two identical heavy chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain and the light chain variable domain is aligned with the variable domain of the heavy chain. Antibody light chains of any vertebrate species can be assigned to one of two clearly distinct types, namely kappa (κ) and lambda (λ), based on the amino acid sequences of their constant domains.

Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$.

Antibodies are secreted proteins constitutively expressed and secreted by plasma cells. Antibodies can also be produced using plasma cells immortalized by standard methods such as hybridoma generation or by transfection of antibody heavy and/or light chain genes into an immortalized B cell such as a myeloma cell or other cell types, such as Chinese hamster ovary (CHO) cells, plant cells and insect cells.

The term "antibody fragments" means a portion of an intact antibody, generally the antigen binding or variable region of the intact antibody. Examples of antibody fragments include Fab, Fab', $F(ab')_2$ and Fv fragments, diabodies, single chain antibody molecules, such as scFv molecules where the variable heavy and variable light chains are connected as a single polypeptide chain by a linker and multispecific antibodies formed from at least two intact antibodies.

Humanized, human-adapted and CDR-grafted antibodies are chimeric monoclonal antibodies containing CDRs from a non-human species and variable region framework regions and constant regions from a human antibody.

The present invention provides a novel antibody human adaptation method. The method uses human germline V and J genes as a source of acceptor FW sequences, ranks all the acceptor FWs based upon FW similarity and other criteria between non-human antibody and human germline sequences, and generates a library of representative human adapted antibodies (see FIG. 3 flowchart). The algorithms used in the process of the invention are described below.

1. Creation of Virtual Human FW Database

Germline V and J gene sequences were downloaded from VBase (http://vbase_.mrc-cpe_.cam_.ac_.uk/) database. VBase is a comprehensive directory of all human germline variable region sequences compiled from over a thousand published sequences, including those in the current releases of the Genbank and EMBL data libraries. The database has been developed over several years at the MRC Centre for Protein Engineering as an extension of work on the sequencing and mapping of human antibody genes.

Figure 4:
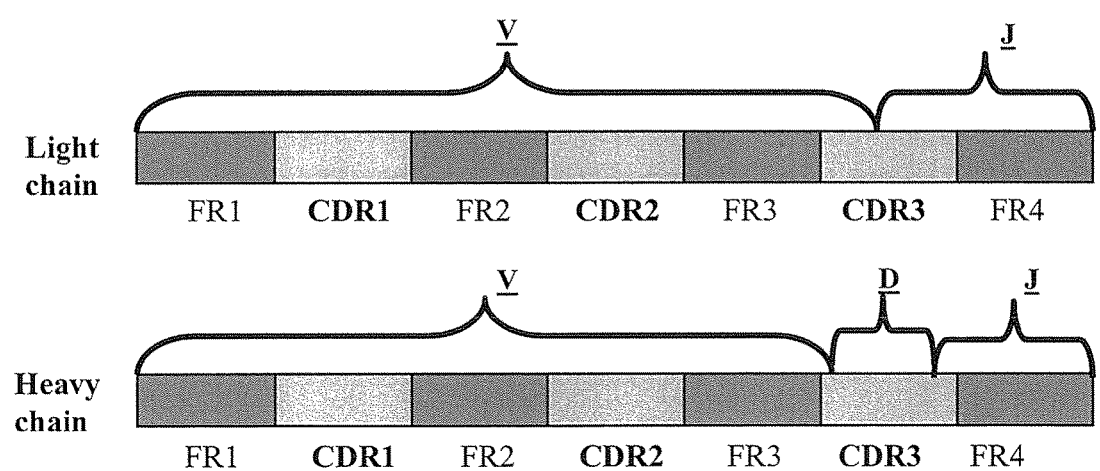
FIG. 4 shows From V,D,J gene fragment to variable FR/CDR.
Figure 9A:
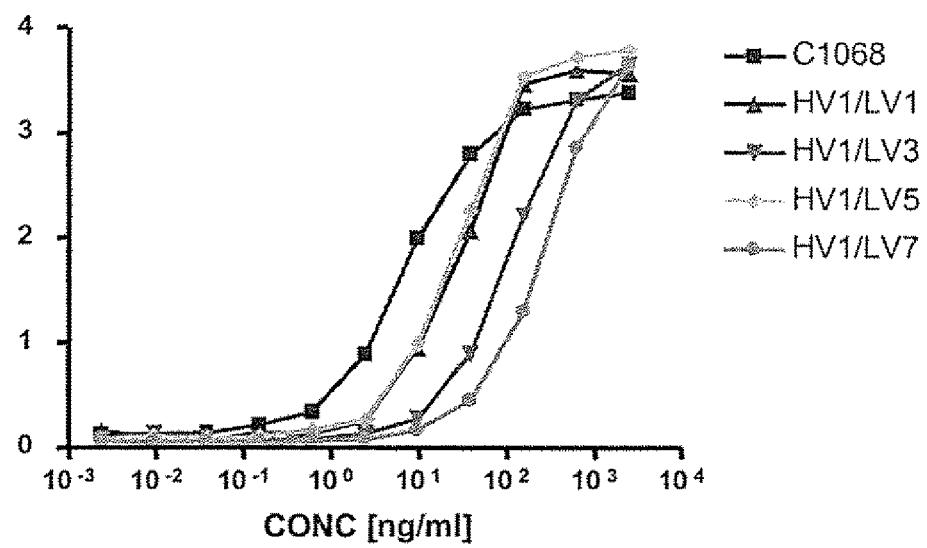
FIGS. 9A, B, C and D shows binding of human-adapted anti-TLR3 mAbs to hTLR3 in ELISA assays.
Figure 9B:
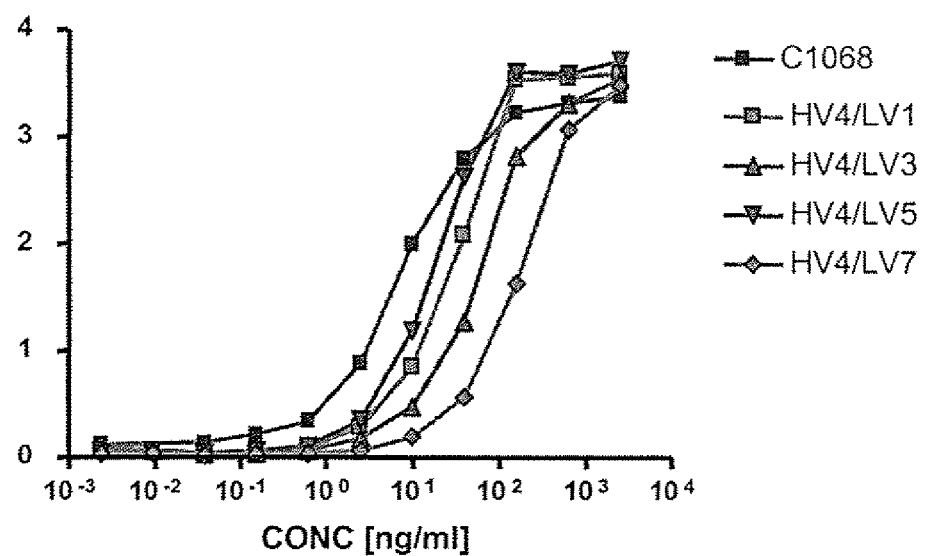
Figure 9C:
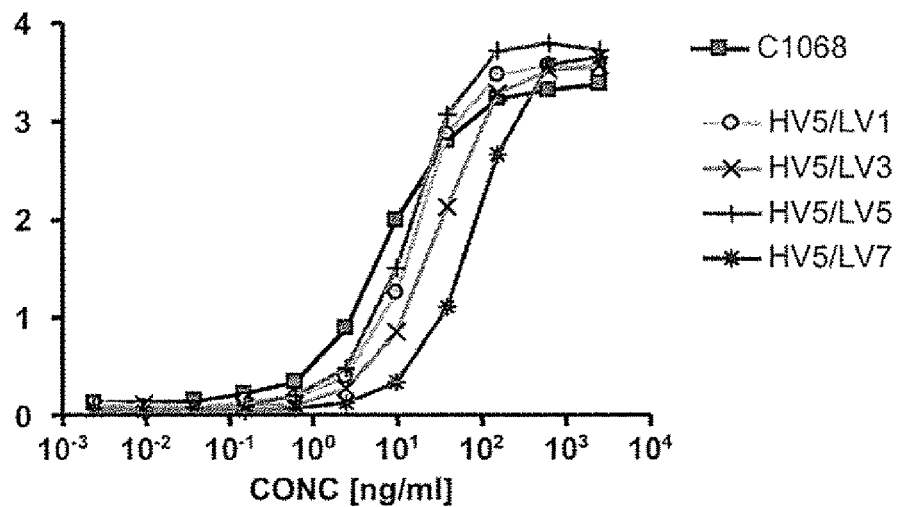
Figure 9D:
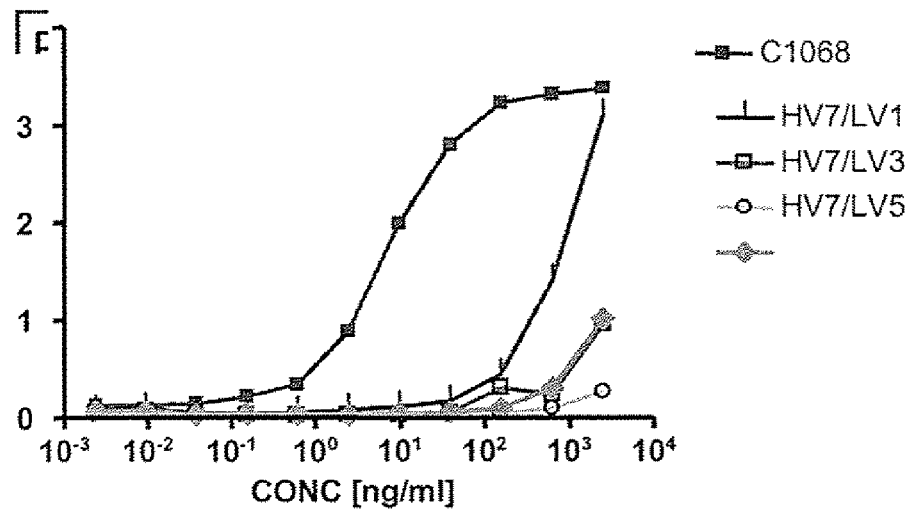

A FW consists of 4 short framework regions (FR). As seen in FIG. 4, FR1, FR2 and FR3 are encoded by the germline V gene fragment, while FR4 is encoded by the germline J gene fragment. In the VBase database, each germline V gene has been delimited into FR and CDR regions. In order to implement the framework library strategy of the invention, a virtual FW database was created from V and J gene sequences. Each record in the virtual FW database consists of 4 fields, i.e., FR1, FR2, FR3 and FR4, and is generated by exhaustive V/J combination of FRs. For example, in the heavy chain there are 6 J H fragments, but they encode only 4 unique FR4 fragments (due to JH1, JH4 and JH5 encoding the same FR4), see FIG. 2. The last 11 residues from each J H sequence correspond to FR4. The pairing of all the FR1-FR2-FR3 from heavy germline V genes with these 4 unique FR4 generated the FW database for the heavy chain. The FW database for kappa and lambda light chains was similarly generated.

There are a total of 666 records in the resultant FW database, of which 260 are generated from germline heavy chains, and 190 and 216 are from kappa and lambda light chains, respectively. There are no redundant entries in the FW database, and each FW record is unique.

2. Delineation of an Antibody Sequence into FRs and CDRs

The Kabat CDR definition, which is based upon antibody sequence variability, is commonly used in sequence delineation. Other known rules or patterns (http://www_.bioinf_.org_.uk/abs/index._html) are also typically applied to find the CDRs in an antibody sequence, but it is not uncommon that many antibody CDRs do not conform to the patterns. Compared to CDRs, FRs are much more conserved in terms of length and homology. Instead of finding CDRs directly, the method of the invention uses the algorithm described below to identify FRs, and accordingly, the corresponding CDRs are deduced (see FIG. 4 for antibody FR/CDR decomposition).

The FW database constructed as described above contains FR1, FR2, FR3 and FR4 sequences for each FW. For a given antibody sequence and its compatible germline FW, the algorithm identifies the frame regions (i.e., FR1, FR2, FR3 and FR4 sequences) as follows. Taking FR2 as an example, a FR2 window deduced from the human germline sequence is moved along antibody sequence starting from the first residue, and the similarity for the sequences in the window is calculated at every residue position. When the FR2 window sequence matches its antibody counterpart sequence, a high similarity peak will be observed, thus identifying FR2. Likewise, FR1, FR3 and FR4 can be found in a similar manner. This algorithm is very effective at identifying the frame regions and universally applicable to any antibody sequence.

3. Novel Fragment-Based Homology and Framework Database Filtering

In CDR-grafting, a rodent donor antibody FW is replaced with a human one, and the CDRs remain the same. However, the length of each FR in the rodent antibody must be compatible with that in the human FR. After a donor antibody sequence is delineated into FR and CDR regions, its FRs are compared with each FW in the database created above. This generates a list of FWs ranked by their similarities to the donor antibody. The homology comparison algorithm of the invention is detailed as below.

First, FR length compatibility between the non-human antibody FRs and human FRs is checked and a subset of human sequences having an identical length to the non-human FRs are selected. For example, in FR1, there are always 30 residues in this region for heavy chain, while the numbers are always 22 and 23 for lambda and kappa chains, respectively. If a given antibody is a kappa light chain, only those kappa FWs in the database can be chosen; it's not possible to choose a lambda FW since the length of FR1 between donor and acceptor are not identical, though it is very likely that the donor kappa sequence is very similar to a lambda germline as a whole. This novel homology comparison algorithm is expected to significantly reduce the false positives in the choice of FWs.

Next, if an acceptor FW passes the check of FR length compatibility, the number of residue differences between donor and acceptor FWs are counted, and then the overall sequence similarity between donor and acceptor FW sequences is calculated. If the similarity is below a threshold value called the identity_threshold value, the corresponding FW is skipped/omitted. The identity_threshold is a user-specified parameter, and the default values are at least 60% for both the heavy and light chain. The purpose of this parameter is to reduce the number of candidate FWs so that only FWs with reasonable similarity to donor could be selected for CDR-grafting.

Next, the CDR1 and CDR2 length compatibility between the selected human peptide sequences and the peptide sequences of the non-human framework regions are compared. Specifically, CDR1 length is compared and a value reflecting the number of residues that differ is generated. Likewise, CDR2 length is compared and a similar value generated. The CDR1 and CDR2 length difference values are added together to generate a CDR12 length compatibility value. The framework having its CDR12_length_compatibility value greater than a CDR12_length_compatibility_threshold value is eliminated. The recommended CDR12_length_compatibility_threshold value is 0 or 1.

Finally, all candidate FWs identified from the length comparison, sequence homology and CDR12 length comparison of the virtual FW database are sorted based upon FW sequence identity so that the most homologous FW is ranked first.

4. Selection of Representative FWs for Screening

Under certain circumstances, it may be desirable to screen a smaller representative library of candidate FWs rather than the entire candidate set. First, some FWs are too similar to each other with even a single residue difference due to the intrinsic close similarity among some germline sequences. Under this circumstance, it's reasonable and beneficial not to include all such FWs for screening, and choose one representative FW instead. Second, wet labs may not have the capacity to screen all the combined FWs if the resultant library is too big. For example, if the FW similarity thresholds is set to a default 60% (for heavy chain) and 70% (for light chain), 75 and 80 candidate FWs were obtained for a mouse anti-TLR3 mAb heavy and light chains, respectively (See FIGS. 5 and 6 and Example 1, infra). The total number of HC/LC FW combinations is 6000, and this poses a great challenge for wet-lab screening.

In the present invention, an algorithm has been developed to automate the choice of representative FWs, and generate a much smaller and less redundant FW library for screening. A user can input the FW library size (number of members) and the FW redundant criterion (Redundant_Threshold), and the algorithm automatically compares all candidate FWs and creates the FW library accordingly. The choice of FW redundant criterion is dependant upon the total number of the candidate FWs after homology comparison and the desired size of FW library for screening. In practice, a 1 to 3 residue difference is recommended. FW library size can be any integer, e.g., 4 to 20. The algorithm steps and parameters are detailed below.

Algorithm parameters:

Candidate_FW_List: all the candidate FWs after homology comparison;
Output_FW_List: the list of FW library sequence;
Library_Size: the size of FW library;
Redundant_Threshold: the criterion for considering two FWs to be redundant;
Active_FW: the current chosen FW from Candidate_FW_List
Flowchart:

a. Check the size of Candidate_FW_List, go to step f) if this list is empty;
b. Choose the first FW from Candidate_FW_List;
  i. set this FW to Active_FW;
  ii. remove it from Candidate_FW_List;
  iii. put it into Output_FW_List;
c. Check the size of Output_FW_List, go to step f) if Library_Size is reached;
d. Count the residue difference between each FW in Candidate_FW_List with Active_FW, remove this FW from Candidate_FW_List if the difference is below Redundant_Threshold;
e. Go to step a)
f. Graft CDRs of rodent antibody into each FW in Output_FW_List; and stop.

Output:

A library of representative humanized antibodies.

The algorithm defined above can be modified to change the size of FW library so as to match wet-lab screening capacity. For rodent antibody heavy and light chains, the corresponding FW libraries will be generated respectively, and all the human adapted heavy and light chains will be combined for screening. Thus, the overall FW library strategy algorithm of the invention increases the likelihood of finding favorable pairs of human heavy and light chains with optimal interchain interactions that are likely important for affinity retention.

One of ordinary skill in the art could automate the key steps of the algorithm through computer programming, such as in object-oriented Java language. Useful import/export functions include the ability to read rodent antibody sequences in a variety of formats and write out FW library sets in flat Fasta files or export them into a spreadsheet or HTML file.

After the selection of favorable pairs of human heavy and light chain frameworks by the methods of the invention, a chimeric molecule can be constructed that includes each of the CDR regions from the non-human variable region and framework regions from at least one member of the human heavy and light chain representative frameworks selected, wherein the chimeric molecule is a human-adapted antibody or antibody fragment that binds the same antigen as that bound by the non-human antibody. Recombinant DNA techniques well-known to those skilled in the art can be used to construct the chimeric molecules. The chimeric molecules can then be selected by screening each molecule for binding affinity to antigen and selecting the optimal human-adapted antibody or antibody fragment.

The method of the invention provides a number of advantages over current human adaptation techniques. For example, in contrast to all other structure-based strategies, such as SDR-grafting, the method of the invention does not require detailed antibody or antigen-antibody complex structure information. Another advantage of the method of the invention is that it can provide several comparable, yet distinct humanized antibodies for the same CDR donor. This is especially useful for therapeutic antibody development, enabling researchers to select a lead candidate and have one or more follow-on or backup candidates.

Another related advantage of the method of the invention is that these comparable candidates, with their distinct sequences, may have different chemical, physiological, and pharmaceutical properties. This can be utilized in other aspects of therapeutic antibody improvement. For example, the CDRs of antibody with low solubility can be fitted to a human framework library, and a good binder with improved solubility may be selected from the resulting antibodies.

The present invention will now be described with reference to the following specific, non-limiting examples.

EXAMPLE 1

Human Adaptation of a Murine Monoclonal Antibody

The amino acid sequences of the murine anti-TLR3 mAb C1068 heavy (HC) and light chains (LC) are listed in FIGS. 5 and 6, respectively. Application of the framework library humanization strategy algorithm of the invention discussed to mAb C1068 generated a FW library set of 8 HC and 12 LC. 4 HC and 4 LC were picked for initial screening.

The similarity between each FW and mAb C1068 is reported in Table 1. The results indicate that all of the 4 HC and 4 LC are comparable in terms of overall sequence similarity. Multiple sequence alignment of the 4 HC shows that these 4 FWs are very similar to each other (FIG. 7), and this holds true for the 4 LC FWs (see FIG. 8 for multiple FW sequence alignment) as well.

TABLE 1

Framework library for murine anti-TLR3 mAb C1068

| Heavy chain FW library | | | Light chain FW library | | |
|---|---|---|---|---|---|
| Abbr. | FW | Identity (%) | Abbr. | FW | Identity (%) |
| HV1 | VB_1-03/JH1 | 72 | LV1 | VB_O12/JK2 | 78 |
| HV4 | VB_1-02/JH1 | 71 | LV3 | VB_A30/JK2 | 77 |
| HV5 | VB_1-08/JH1 | 71 | LV5 | VB_A20/JK4 | 76 |
| HV7 | VB_1-69/JH2 | 71 | LV7 | VB_L1/JK2 | 76 |

Sixteen mAbs representing all possible combinations of the four heavy and four light chain variable region constructs were expressed. All heavy chain variable region frameworks were expressed with a human IgG4 heavy chain constant region having a Ser to Pro substitution at residue 108 and Phe114 and Leu115 to Ala substitutions; S228P, F234A and L235A in the full-length heavy chain. All light chain variable region frameworks were expressed using a human K constant region. Antibodies were expressed transiently in mammalian cells by co-transfection of appropriate heavy and light chain containing plasmids. Antibodies were purified using standard protein A purification and dialyzed into PBS for characterization.

All 16 mAbs were assessed for binding to the extracellular domain of human TLR3 using an ELISA format as compared to the parental murine mAb C1068. Briefly, soluble human TLR3 extracellular domain was coated into the wells of a 96 well plate and candidate mAbs were incubated at various concentrations (10-3 to 103 ng/ml) and bound antibody was detected with rabbit anti-mouse IgG-HRP for murine IgG1 isotypes (Zymed, South San Francisco, Calif.) or HRP-labeled anti-human IgG (Jackson 109-036-088) for human IgG4 isotypes. $EC_{50}$ values were determined and the screening results are shown in FIG. 9 and Table 2 below.

TABLE 2

Calculated $EC_{50}$ values for 16 combinatorial mAbs

| $EC_{50}$ ng/ml | HV1 | HV4 | HV5 | HV7 |
|---|---|---|---|---|
| LV1 | 29.2 | 29.1 | 15.5 | 1474.0 |
| LV3 | 117.7 | 60.2 | 28.9 | >5000 |
| LV5 | 27.7 | 18.7 | 13.7 | 1820.0 |
| LV7 | 288.8 | 182.9 | 78.6 | 4258.0 |

The calculated $EC_{50}$ for C1068 was 8 ng/ml; the results indicated that 12 of the human-adapted mAbs had less than a 40-fold reduction in calculated $EC_{50}$ relative to the murine parent mAb 1068. Pairs LV5/HV5, LV5/LV4, and LV1/HV5 are better than the most homologous pair LV1/HV1 in terms of affinity.

The affinity data in Table 2 and FIG. 9 clearly show that, at least in the case of anti-TLR3 antibody, the best-fit choice is not the best acceptor, and that interchain interactions contribute to antibody affinity. Our novel human framework library strategy and algorithm, therefore, fundamentally challenges the traditional best-fit approach, and at the same time provides a very promising experimental approach, for the selection of acceptors for antibody humanization.

The present invention now being fully described, it will be apparent to one of ordinary skill in the art that many changes and modifications can be made thereto without departing from the spirit or scope of the appended claims.

The invention claimed is:

1. A method for selecting human antibody frameworks for use in making a human-adapted antibody comprising the steps of:
   a. obtaining a peptide sequence for a variable region of a non-human antibody;
   b. delineating the peptide sequences of the complementarity determining regions (CDRs) and framework regions of the non-human variable region;
   c. constructing a library of peptide sequences for human antibody framework 1, 2, 3 and 4 regions encoded by human germline genes;
   d. selecting a subset of member human peptide sequences from the library having an identical length to the framework regions of the non-human mature antibody;
   e. comparing the frame region sequence similarity of the selected human peptide sequences to the peptide sequences of the non-human framework regions;
   f. comparing the CDR1 and CDR2 length compatibility between the selected human peptide sequences and the peptide sequences of the non-human framework regions;
   g. selecting a second subset of the selected human peptide sequences wherein the peptide sequences selected have a frame region similarity of greater than an identity_threshold value and the sum of the length difference of CDR1 and CDR2 is smaller than or equal to a CDR12_length_compatibility_threshold value; and
   h. selecting representative frameworks from the second subset of step g) based upon a library_size value and a framework_region_redundancy value.

2. A method of making a human-adapted antibody or antibody fragment comprising the steps of:
   a. obtaining a peptide sequence for a variable region of a non-human antibody;
   b. delineating the peptide sequences of the complementarity determining regions (CDRs) and framework regions of the non-human variable region;
   c. constructing a library of peptide sequences for human antibody framework 1, 2, 3 and 4 regions encoded by human germline genes;
   d. selecting a subset of member human peptide sequences from the library having an identical length to the framework regions of the non-human mature antibody;
   e. comparing the frame region sequence similarity of the selected human peptide sequences to the peptide sequences of the non-human framework regions;
   f. comparing the CDR1 and CDR2 length compatibility between the selected human peptide sequences and the peptide sequences of the non-human framework regions;
   g. selecting a second subset of the selected human peptide sequences wherein the peptide sequences selected have a frame region similarity of greater than an identity_threshold value and the sum of the length difference of CDR1 and CDR2 is smaller than or equal to a CDR12_length_compatibility_threshold value;
   h. selecting representative frameworks from the second subset of step g) based upon a library_size value and a framework_region_redundancy value; and
   i. constructing a chimeric molecule that includes each of the CDR regions from the non-human variable region and framework regions from at least one member of the human heavy and light chain representative frameworks selected in step h), wherein the chimeric molecule is a human-adapted antibody or antibody fragment that binds the same antigen as that bound by the non-human antibody.

3. The method of claim 2 further comprising the step of:
   i. screening each combination for binding affinity to antigen and selecting the optimal human-adapted antibody or antibody fragment.

4. The method of claim 1 or 2 wherein the identity_threshold value is at least 60% for the heavy and light chain frameworks.

5. The method of claim 1 or 2 wherein the CDR12_length_compatibility value is 0 or 1.

6. The method of claim 1 or 2 wherein the library_size value is 4 to 20.

7. The method of claim 1 or 2 wherein the framework_region_redundancy value is 1 to 3.

* * * * *

SEQUENCE LISTING

<160> NUMBER OF SEQ ID NOS: 57

<210> SEQ ID NO 1
<211> LENGTH: 119
<212> TYPE: PRT
<213> ORGANISM: Homo sapiens

<400> SEQUENCE: 1

Gln Val Gln Leu Gln Gln Pro Gly Ala Glu Leu Val Gln Pro Gly Thr
1               5                   10                  15

Ser Val Arg Leu Ser Cys Lys Ala Ser Gly Tyr Ile Phe Thr Thr Tyr
            20                  25                  30

Trp Ile His Trp Val Lys Gln Arg Pro Gly Gln Gly Leu Glu Trp Ile
        35                  40                  45

Gly Glu Ile Asn Pro Asn Asn Gly Arg Ile Asn Tyr Asn Glu Lys Phe
    50                  55                  60

Lys Thr Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Val Gly Val Met Ile Thr Thr Phe Pro Tyr Trp Gly Gln Gly
            100                 105                 110

Thr Leu Val Thr Val Ser Ala
        115

<210> SEQ ID NO 2
<211> LENGTH: 107
<212> TYPE: PRT
<213> ORGANISM: Homo sapiens

<400> SEQUENCE: 2

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Glu Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Phe
                85                  90                  95

Thr Phe Gly Ser Gly Thr Lys Leu Glu Leu Lys
            100                 105

<210> SEQ ID NO 3
<211> LENGTH: 119
<212> TYPE: PRT
<213> ORGANISM: Artificial Sequence
<220> FEATURE:
<223> OTHER INFORMATION: Human-adapted heavy chain HV1

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Ile His Trp Val Arg Gln Ala Pro Gly Gln Arg Leu Glu Trp Met
            35                  40                  45

Gly Glu Ile Asn Pro Asn Asn Gly Arg Ile Asn Tyr Asn Glu Lys Phe
 50                  55                  60

Lys Thr Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Val Gly Val Met Ile Thr Thr Phe Pro Tyr Trp Gly Gln Gly
                100                 105                 110

Thr Leu Val Thr Val Ser Ser
            115

<210> SEQ ID NO 4
<211> LENGTH: 119
<212> TYPE: PRT
<213> ORGANISM: Artificial Sequence
<220> FEATURE:
<223> OTHER INFORMATION: Human-adapted heavy chain HV4

<400> SEQUENCE: 4

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
                 20                  25                  30

Trp Ile His Trp Val Arg Gln Ala Pro Gly Gln Gly Leu Glu Trp Met
            35                  40                  45

Gly Glu Ile Asn Pro Asn Asn Gly Arg Ile Asn Tyr Asn Glu Lys Phe
 50                  55                  60

Lys Thr Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Val Gly Val Met Ile Thr Thr Phe Pro Tyr Trp Gly Gln Gly
                100                 105                 110

Thr Leu Val Thr Val Ser Ser
            115

<210> SEQ ID NO 5
<211> LENGTH: 119
<212> TYPE: PRT
<213> ORGANISM: Artificial Sequence
<220> FEATURE:
<223> OTHER INFORMATION: Human-adapted heavy chain HV5

<400> SEQUENCE: 5

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
                 20                  25                  30

Trp Ile His Trp Val Arg Gln Ala Thr Gly Gln Gly Leu Glu Trp Met
            35                  40                  45

Gly Glu Ile Asn Pro Asn Asn Gly Arg Ile Asn Tyr Asn Glu Lys Phe
 50                  55                  60

Lys Thr Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

```
Ala Arg Val Gly Val Met Ile Thr Thr Phe Pro Tyr Trp Gly Gln Gly
            100                 105                 110

Thr Leu Val Thr Val Ser Ser
        115

<210> SEQ ID NO 6
<211> LENGTH: 119
<212> TYPE: PRT
<213> ORGANISM: Artificial Sequence
<220> FEATURE:
<223> OTHER INFORMATION: Human-adapted heavy chain HV7

<400> SEQUENCE: 6

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Thr Tyr
            20                  25                  30

Trp Ile His Trp Val Arg Gln Ala Pro Gly Gln Gly Leu Glu Trp Met
        35                  40                  45

Gly Glu Ile Asn Pro Asn Asn Gly Arg Ile Asn Tyr Asn Glu Lys Phe
50                  55                  60

Lys Thr Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Val Met Ile Thr Thr Phe Pro Tyr Trp Gly Arg Gly
            100                 105                 110

Thr Leu Val Thr Val Ser Ser
        115

<210> SEQ ID NO 7
<211> LENGTH: 107
<212> TYPE: PRT
<213> ORGANISM: Artificial Sequence
<220> FEATURE:
<223> OTHER INFORMATION: Human-adapted heavy chain LV1

<400> SEQUENCE: 7

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Ser Thr Pro Phe
                85                  90                  95

Thr Phe Gly Gln Gly Thr Lys Leu Glu Ile Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: Human-adapted heavy chain LV3
```

-continued

```
<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Ala Pro Lys Arg Leu Ile
        35                  40                  45

Tyr Asn Ala Lys Thr Leu Ala Asp Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Phe Trp Ser Thr Pro Phe
                85                  90                  95

Thr Phe Gly Gln Gly Thr Lys Leu Glu Ile Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: Human-adapted heavy chain LV5

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Val Pro Lys Leu Leu Ile
        35                  40                  45

Tyr Asn Ala Lys Thr Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Phe Trp Ser Thr Pro Phe
                85                  90                  95

Thr Phe Gly Gly Gly Thr Lys Val Glu Ile Lys
            100                 105

<210> SEQ ID NO 10
<211> LENGTH: 107
<212> TYPE: PRT
<213> ORGANISM: Artificial Sequence
<220> FEATURE:
<223> OTHER INFORMATION: Human-adapted heavy chain LV7

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ala Trp Phe Gln Gln Lys Pro Gly Lys Ala Pro Lys Ser Leu Ile
        35                  40                  45

Tyr Asn Ala Lys Thr Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Ser Thr Pro Phe
```

```
                    85                  90                  95
Thr Phe Gly Gln Gly Thr Lys Leu Glu Ile Lys
               100                 105

<210> SEQ ID NO 11
<211> LENGTH: 17
<212> TYPE: PRT
<213> ORGANISM: Artificial Sequence
<220> FEATURE:
<223> OTHER INFORMATION: Polypeptide fragment encoding JH1 region of
      human antibody germline gene

<400> SEQUENCE: 11

Ala Glu Tyr Phe Gln His Trp Gly Gln Gly Thr Leu Val Thr Val Ser
1               5                   10                  15

Ser

<210> SEQ ID NO 12
<211> LENGTH: 17
<212> TYPE: PRT
<213> ORGANISM: Artificial Sequence
<220> FEATURE:
<223> OTHER INFORMATION: Polypeptide fragment encoding JH2 region of
      human antibody germline gene

<400> SEQUENCE: 12

Tyr Trp Tyr Phe Asp Leu Trp Gly Arg Gly Thr Leu Val Thr Val Ser
1               5                   10                  15

Ser

<210> SEQ ID NO 13
<211> LENGTH: 15
<212> TYPE: PRT
<213> ORGANISM: Artificial Sequence
<220> FEATURE:
<223> OTHER INFORMATION: Polypeptide fragment encoding JH3 region of
      human antibody germline gene

<400> SEQUENCE: 13

Ala Phe Asp Val Trp Gly Gln Gly Thr Met Val Thr Val Ser Ser
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Polypeptide fragment encoding JH4 region of
      human antibody germline gene

<400> SEQUENCE: 14

Tyr Phe Asp Tyr Trp Gly Gln Gly Thr Leu Val Thr Val Ser Ser
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Polypeptide fragment encoding JH5 region of
      human antibody germline gene

<400> SEQUENCE: 15

Asn Trp Phe Asp Ser Trp Gly Gln Gly Thr Leu Val Thr Val Ser Ser
1               5                   10                  15
```

```
<210> SEQ ID NO 16
<211> LENGTH: 20
<212> TYPE: PRT
<213> ORGANISM: Artificial Sequence
<220> FEATURE:
<223> OTHER INFORMATION: Polypeptide fragment encoding JH6 region of
      human antibody germline gene

<400> SEQUENCE: 16

Tyr Tyr Tyr Tyr Tyr Gly Met Asp Val Trp Gly Gln Gly Thr Thr Val
1               5                   10                  15

Thr Val Ser Ser
            20

<210> SEQ ID NO 17
<211> LENGTH: 14
<212> TYPE: PRT
<213> ORGANISM: Artificial Sequence
<220> FEATURE:
<223> OTHER INFORMATION: FRAGMENT OF HUMAN eu MYELOMA PROTEIN

<400> SEQUENCE: 17

Ser Pro Glu Glu Tyr Asn Gly Gly Leu Val Thr Val Ser Ser
1               5                   10

<210> SEQ ID NO 18
<211> LENGTH: 14
<212> TYPE: PRT
<213> ORGANISM: Artificial Sequence
<220> FEATURE:
<223> OTHER INFORMATION: VJ region sequence of mouse anti-Tac antibody

<400> SEQUENCE: 18

Phe Asp Tyr Trp Gly Gln Gly Thr Thr Leu Thr Val Ser Ser
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Fragment Encoding VJ Region Of Humanized
      Anti-Tac Antibody

<400> SEQUENCE: 19

Phe Asp Tyr Trp Gly Gln Gly Thr Leu Val Thr Val Ser Ser
1               5                   10

<210> SEQ ID NO 20
<211> LENGTH: 30
<212> TYPE: PRT
<213> ORGANISM: Artificial Sequence
<220> FEATURE:
<223> OTHER INFORMATION: Heavy Chain FR1 Region Of Antibody 1068

<400> SEQUENCE: 20

Gln Val Gln Leu Gln Gln Pro Gly Ala Glu Leu Val Gln Pro Gly Thr
1               5                   10                  15

Ser Val Arg Leu Ser Cys Lys Ala Ser Gly Tyr Ile Phe Thr
            20                  25                  30

<210> SEQ ID NO 21
<211> LENGTH: 5
<212> TYPE: PRT
<213> ORGANISM: Artificial Sequence
<220> FEATURE:
<223> OTHER INFORMATION: Heavy Chain CDR1 Region Of Antibody 1068
```

```
<400> SEQUENCE: 21

Thr Tyr Trp Ile His
1               5

<210> SEQ ID NO 22
<211> LENGTH: 14
<212> TYPE: PRT
<213> ORGANISM: Artificial Sequence
<220> FEATURE:
<223> OTHER INFORMATION: Heavy Chain FR2 Region Of Antibody 1068

<400> SEQUENCE: 22

Trp Val Lys Gln Arg Pro Gly Gln Gly Leu Glu Trp Ile Gly
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Heavy Chain CDR2 Sequence Of Antibody 1068

<400> SEQUENCE: 23

Glu Ile Asn Pro Asn Asn Gly Arg Ile Asn Tyr Asn Glu Lys Phe Lys
1               5                   10                  15

Thr

<210> SEQ ID NO 24
<211> LENGTH: 32
<212> TYPE: PRT
<213> ORGANISM: Artificial Sequence
<220> FEATURE:
<223> OTHER INFORMATION: HEAVY CHAIN FR3 SEQUENCE OF ANTIBODY 1068

<400> SEQUENCE: 24

Lys Ala Thr Leu Thr Val Asp Lys Ser Ser Ser Thr Ala Tyr Met Gln
1               5                   10                  15

Leu Ser Ser Leu Thr Ser Glu Asp Ser Ala Val Tyr Tyr Cys Thr Arg
                20                  25                  30

<210> SEQ ID NO 25
<211> LENGTH: 10
<212> TYPE: PRT
<213> ORGANISM: Artificial Sequence
<220> FEATURE:
<223> OTHER INFORMATION: Heavy Chain CDR3 Sequence Of Antibody 1068

<400> SEQUENCE: 25

Val Gly Val Met Ile Thr Thr Phe Pro Tyr
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Heavy Chain FR4 Sequence Of Antibody 1068

<400> SEQUENCE: 26

Trp Gly Gln Gly Thr Leu Val Thr Val Ser Ala
1               5                   10

<210> SEQ ID NO 27
<211> LENGTH: 23
<212> TYPE: PRT
<213> ORGANISM: Artificial Sequence
```

```
<220> FEATURE:
<223> OTHER INFORMATION: Light Chain FR1 Sequence Of Antibody 1068

<400> SEQUENCE: 27

Asp Ile Gln Met Thr Gln Ser Pro Ala Ser Leu Ser Ala Ser Val Gly
1               5                   10                  15

Glu Thr Val Thr Ile Thr Cys
            20

<210> SEQ ID NO 28
<211> LENGTH: 11
<212> TYPE: PRT
<213> ORGANISM: Artificial Sequence
<220> FEATURE:
<223> OTHER INFORMATION: Light Chain CDR1 Sequence Of Antibody 1068

<400> SEQUENCE: 28

Arg Ala Ser Gly Asn Ile His Asn Tyr Leu Ala
1               5                   10

<210> SEQ ID NO 29
<211> LENGTH: 15
<212> TYPE: PRT
<213> ORGANISM: Artificial Sequence
<220> FEATURE:
<223> OTHER INFORMATION: Light Chain FR2 Sequence Of Antibody 1068

<400> SEQUENCE: 29

Trp Tyr Gln Gln Lys Gln Gly Lys Ser Pro Gln Leu Leu Val Tyr
1               5                   10                  15

<210> SEQ ID NO 30
<211> LENGTH: 7
<212> TYPE: PRT
<213> ORGANISM: Artificial Sequence
<220> FEATURE:
<223> OTHER INFORMATION: Light Chain CDR2 Sequence Of Antibody 1068

<400> SEQUENCE: 30

Asn Ala Lys Thr Leu Ala Asp
1               5

<210> SEQ ID NO 31
<211> LENGTH: 32
<212> TYPE: PRT
<213> ORGANISM: Artificial Sequence
<220> FEATURE:
<223> OTHER INFORMATION: Light Chain FR3 Sequence Of Antibody 1068

<400> SEQUENCE: 31

Gly Val Pro Ser Arg Phe Ser Gly Ser Glu Ser Gly Thr Gln Tyr Ser
1               5                   10                  15

Leu Lys Ile Asn Ser Leu Gln Pro Glu Asp Phe Gly Ser Tyr Tyr Cys
            20                  25                  30

<210> SEQ ID NO 32
<211> LENGTH: 9
<212> TYPE: PRT
<213> ORGANISM: Artificial Sequence
<220> FEATURE:
<223> OTHER INFORMATION: Light Chain CDR3 Sequence Of Antibody 1068

<400> SEQUENCE: 32

Gln His Phe Trp Ser Thr Pro Phe Thr
1               5
```

```
<210> SEQ ID NO 33
<211> LENGTH: 10
<212> TYPE: PRT
<213> ORGANISM: Artificial Sequence
<220> FEATURE:
<223> OTHER INFORMATION: Light Chain FR4 Sequence Of Antibody 1068

<400> SEQUENCE: 33

Phe Gly Ser Gly Thr Lys Leu Glu Leu Lys
 1               5                  10

<210> SEQ ID NO 34
<211> LENGTH: 30
<212> TYPE: PRT
<213> ORGANISM: Artificial Sequence
<220> FEATURE:
<223> OTHER INFORMATION: Heavy Chain Scaffold HV1, HV4, And HV5 FR1
      Sequence

<400> SEQUENCE: 34

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: Heavy Chain Scaffold HV7 FR1 Sequence

<400> SEQUENCE: 35

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser
            20                  25                  30

<210> SEQ ID NO 36
<211> LENGTH: 14
<212> TYPE: PRT
<213> ORGANISM: Artificial Sequence
<220> FEATURE:
<223> OTHER INFORMATION: Heavy Chain Scaffold HV1 FR2 Sequence

<400> SEQUENCE: 36

Trp Val Arg Gln Ala Pro Gly Gln Arg Leu Glu Trp Met Gly
 1               5                  10

<210> SEQ ID NO 37
<211> LENGTH: 14
<212> TYPE: PRT
<213> ORGANISM: Artificial Sequence
<220> FEATURE:
<223> OTHER INFORMATION: Heavy Chain Scaffold HV4 FR2 Sequence

<400> SEQUENCE: 37

Trp Val Arg Gln Ala Pro Gly Gln Gly Leu Glu Trp Met Gly
 1               5                  10

<210> SEQ ID NO 38
<211> LENGTH: 14
<212> TYPE: PRT
<213> ORGANISM: Artificial Sequence
<220> FEATURE:
<223> OTHER INFORMATION: Heavy Chain Scaffold HV5 FR2 Sequence

<400> SEQUENCE: 38
```

Trp Val Arg Gln Ala Thr Gly Gln Gly Leu Glu Trp Met Gly
1               5                   10

<210> SEQ ID NO 39
<211> LENGTH: 32
<212> TYPE: PRT
<213> ORGANISM: Artificial Sequence
<220> FEATURE:
<223> OTHER INFORMATION: Heavy Chain Scaffold HV1 FR3 Sequence

<400> SEQUENCE: 39

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 40
<211> LENGTH: 32
<212> TYPE: PRT
<213> ORGANISM: Artificial Sequence
<220> FEATURE:
<223> OTHER INFORMATION: Heavy Chain Scaffold HV4 FR3 Sequence

<400> SEQUENCE: 40

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Heavy Chain Scaffold HV5 FR3 Sequence

<400> SEQUENCE: 41

Arg Val Thr Met Thr Arg Asn Thr Ser Ile Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Heavy Chain Scaffold HV7 FR3 Sequence

<400> SEQUENCE: 42

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 43
<211> LENGTH: 11
<212> TYPE: PRT
<213> ORGANISM: Artificial Sequence
<220> FEATURE:
<223> OTHER INFORMATION: Heavy Chain Scaffold HV1, HV4 And HV5 FR1
      Sequence

<400> SEQUENCE: 43

Trp Gly Gln Gly Thr Leu Val Thr Val Ser Ser

<210> SEQ ID NO 44
<211> LENGTH: 11
<212> TYPE: PRT
<213> ORGANISM: Artificial Sequence
<220> FEATURE:
<223> OTHER INFORMATION: Heavy Chain Scaffold HV7 FR1 Sequence

<400> SEQUENCE: 44

Trp Gly Arg Gly Thr Leu Val Thr Val Ser Ser
1               5                   10

<210> SEQ ID NO 45
<211> LENGTH: 23
<212> TYPE: PRT
<213> ORGANISM: Artificial Sequence
<220> FEATURE:
<223> OTHER INFORMATION: Light Chain Scaffold LV1 LV3, LV5, And LV7 FR1
      Sequence

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 46
<211> LENGTH: 15
<212> TYPE: PRT
<213> ORGANISM: Artificial Sequence
<220> FEATURE:
<223> OTHER INFORMATION: Light Chain Scaffold LV1 FR2 Sequence

<400> SEQUENCE: 46

Trp Tyr Gln Gln Lys Pro Gly Lys Ala Pro Lys Leu Leu Ile Tyr
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Light Chain Scaffold LV3 FR2 Sequence

<400> SEQUENCE: 47

Trp Tyr Gln Gln Lys Pro Gly Lys Ala Pro Lys Arg Leu Ile Tyr
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: LIGHT CHAIN SCAFFOLD LV5 FR2 SEQUENCE

<400> SEQUENCE: 48

Trp Tyr Gln Gln Lys Pro Gly Lys Val Pro Lys Leu Leu Ile Tyr
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Light Chain Scaffold LV7 FR2 Sequence

<400> SEQUENCE: 49

```
Trp Phe Gln Gln Lys Pro Gly Lys Ala Pro Lys Ser Leu Ile Tyr
 1               5                  10                  15

<210> SEQ ID NO 50
<211> LENGTH: 32
<212> TYPE: PRT
<213> ORGANISM: Artificial Sequence
<220> FEATURE:
<223> OTHER INFORMATION: Light Chain Scaffold LV1 And LV7 FR3 Sequence

<400> SEQUENCE: 50

Gly Val Pro Ser Arg Phe Ser Gly Ser Gly Ser Gly Thr Asp Phe Thr
 1               5                  10                  15

Leu Thr Ile Ser Ser Leu Gln Pro Glu Asp Phe Ala Thr Tyr Tyr Cys
                20                  25                  30

<210> SEQ ID NO 51
<211> LENGTH: 32
<212> TYPE: PRT
<213> ORGANISM: Artificial Sequence
<220> FEATURE:
<223> OTHER INFORMATION: Light Chain Scaffold LV3 FR3 Sequence

<400> SEQUENCE: 51

Gly Val Pro Ser Arg Phe Ser Gly Ser Gly Ser Gly Thr Glu Phe Thr
 1               5                  10                  15

Leu Thr Ile Ser Ser Leu Gln Pro Glu Asp Phe Ala Thr Tyr Tyr Cys
                20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Light Chain Scaffold LV5 FR3 Sequence

<400> SEQUENCE: 52

Gly Val Pro Ser Arg Phe Ser Gly Ser Gly Ser Gly Thr Asp Phe Thr
 1               5                  10                  15

Leu Thr Ile Ser Ser Leu Gln Pro Glu Asp Val Ala Thr Tyr Tyr Cys
                20                  25                  30

<210> SEQ ID NO 53
<211> LENGTH: 10
<212> TYPE: PRT
<213> ORGANISM: Artificial Sequence
<220> FEATURE:
<223> OTHER INFORMATION: Light Chain Scaffold Of LV1, LV3, And LV7 FR4
      Sequence

<400> SEQUENCE: 53

Phe Gly Gln Gly Thr Lys Leu Glu Ile Lys
 1               5                  10

<210> SEQ ID NO 54
<211> LENGTH: 10
<212> TYPE: PRT
<213> ORGANISM: Artificial Sequence
<220> FEATURE:
<223> OTHER INFORMATION: Light Chain Scaffold Of LV5 FR4 Sequence

<400> SEQUENCE: 54

Phe Gly Gly Gly Thr Lys Val Glu Ile Lys
 1               5                  10
```

```
<210> SEQ ID NO 55
<211> LENGTH: 10
<212> TYPE: PRT
<213> ORGANISM: Artificial Sequence
<220> FEATURE:
<223> OTHER INFORMATION: Fragment of human antibody germline gene JH4
      region

<400> SEQUENCE: 55

Phe Asp Tyr Trp Gly Gln Gly Thr Leu Val Thr Val Ser Ser
 1               5                  10

<210> SEQ ID NO 56
<211> LENGTH: 138
<212> TYPE: PRT
<213> ORGANISM: Artificial Sequence
<220> FEATURE:
<223> OTHER INFORMATION: Heavy Chain Variable Region

<400> SEQUENCE: 56

Met Gly Trp Ser Tyr Ile Ile Leu Phe Leu Val Ala Thr Ala Thr Asp
 1               5                  10                  15

Val His Ser Gln Val Gln Leu Gln Gln Pro Gly Ala Glu Leu Val Gln
                20                  25                  30

Pro Gly Thr Ser Val Arg Leu Ser Cys Lys Ala Ser Gly Tyr Ile Phe
             35                  40                  45

Thr Thr Tyr Trp Ile His Trp Val Lys Gln Arg Pro Gly Gln Gly Leu
         50                  55                  60

Glu Trp Ile Gly Glu Ile Asn Pro Asn Asn Gly Arg Ile Asn Tyr Asn
 65                  70                  75                  80

Glu Lys Phe Lys Thr Lys Ala Thr Leu Thr Val Asp Lys Ser Ser Ser
                 85                  90                  95

Thr Ala Tyr Met Gln Leu Ser Ser Leu Thr Ser Glu Asp Ser Ala Val
                100                 105                 110

Tyr Tyr Cys Thr Arg Val Gly Val Met Ile Thr Thr Phe Pro Tyr Trp
            115                 120                 125

Gly Gln Gly Thr Leu Val Thr Val Ser Ala
        130                 135

<210> SEQ ID NO 57
<211> LENGTH: 127
<212> TYPE: PRT
<213> ORGANISM: Artificial Sequence
<220> FEATURE:
<223> OTHER INFORMATION: Light Chain Variable Region

<400> SEQUENCE: 57

Met Ser Val Leu Thr Gln Val Leu Ala Leu Leu Leu Leu Trp Leu Thr
 1               5                  10                  15

Gly Ala Arg Cys Asp Ile Gln Met Thr Gln Ser Pro Ala Ser Leu Ser
                20                  25                  30

Ala Ser Val Gly Glu Thr Val Thr Ile Thr Cys Arg Ala Ser Gly Asn
             35                  40                  45

Ile His Asn Tyr Leu Ala Trp Tyr Gln Gln Lys Gln Gly Lys Ser Pro
         50                  55                  60

Gln Leu Leu Val Tyr Asn Ala Lys Thr Leu Ala Asp Gly Val Pro Ser
 65                  70                  75                  80

Arg Phe Ser Gly Ser Glu Ser Gly Thr Gln Tyr Ser Leu Lys Ile Asn
                 85                  90                  95

Ser Leu Gln Pro Glu Asp Phe Gly Ser Tyr Tyr Cys Gln His Phe Trp
                100                 105                 110
```

```
Ser Thr Pro Phe Thr Phe Gly Ser Gly Thr Lys Leu Glu Leu Lys
    115             120             125
```